United States Patent [19]
Patko et al.

[11] Patent Number: 6,153,085
[45] Date of Patent: Nov. 28, 2000

[54] INFORMATION STORAGE AND TRANSMITTAL FOR MEDICAL DIAGNOSTIC DEVICES

[75] Inventors: Martin J. Patko, Orange; Michael H. Burnam, Hidden Hills, both of Calif.

[73] Assignee: STAT-Chem, Inc., Orange, Calif.

[21] Appl. No.: 09/135,714

[22] Filed: Aug. 17, 1998

[51] Int. Cl.[7] ............................ G01N 27/26; G01N 27/00
[52] U.S. Cl. .................. 205/775; 422/82.01; 422/82.03; 204/406; 204/400; 204/416; 204/412; 205/789; 702/23
[58] Field of Search ............................. 422/82.01, 82.03, 422/82.04; 204/406, 416, 412, 413, 417, 418; 205/775, 789; 702/22, 23

[56] References Cited

U.S. PATENT DOCUMENTS

| | | | |
|---|---|---|---|
| 4,225,410 | 9/1980 | Pace | 204/412 |
| 5,098,545 | 3/1992 | Patko | 204/403 |
| 5,384,028 | 1/1995 | Ito | 204/403 |
| 5,690,893 | 11/1997 | Ozawa et al. | 422/67 |

FOREIGN PATENT DOCUMENTS

| | | |
|---|---|---|
| 0 351 516 A2 | 1/1990 | European Pat. Off. . |
| 0 450 202 A1 | 10/1991 | European Pat. Off. . |

*Primary Examiner*—Jill Warden
*Assistant Examiner*—Alex Noguerola
*Attorney, Agent, or Firm*—Knobbe Martens Olson & Bear, LLP

[57] ABSTRACT

An electronic sensor is described that includes a sample receptacle and a data storage device. The data storage device is powered by a pair of half cells on the sensor. The half cells contain ion solutions that are also used to calibrate the sensor. As the sensor is placed within a sensor data reader, the data stored on the data storage device is transferred to the reader along with measurements of the voltage potential between the half cells. The reader thereafter calculates a calibration slope curve for the sensor. The calibration slope curve is then used to determine the exact ion concentration of any sample that is placed in the sample receptacle.

15 Claims, 6 Drawing Sheets

INFORMATION STORAGE AND TRANSMITTAL FOR MEDICAL DIAGNOSTIC DEVICES

BACKGROUND OF THE INVENTION

1. Field of the Invention

This invention relates to sensors for determining the ion concentration in a sample. More specifically, this invention relates to sensors with integrated data storage devices that store data for calibrating the sensor.

2. Description of the Related Technology

The medical diagnostics industry is rapidly shifting toward disposable and precalibrated in vitro diagnostic devices. These devices are inexpensive, generally utilize simple instrumentation, and the tests employing these devices may be performed at the point of care by personnel who are less trained than those who conduct the same tests in a clinical environment using complex equipment.

While the simplicity of the testing is welcome, these devices must compete with the results provided by complex equipment in the clinical laboratories in terms of accuracy and reproducibility. These characteristics generally result from a two point calibration of the sensors utilized in the clinical laboratories. Such precise calibration has not been possible or practical for typical diagnostic devices utilizing precalibrated disposable sensors, which typically employ one-point calibration.

Electrochemical sensors function to measure the presence of an ion in a solution. Examples of ions are: calcium, chloride, hydrogen, lithium, magnesium, potassium and sodium. The actual quantitative measurement of the ion concentration is based on the fact that solutions of different ionic strength, if separated by a membrane, create an electrical potential across the membrane. Ion-selective membranes finction by competitive displacement, wherein an ion of interest in a test solution displaces an ion from a ligand embedded within the membrane. The difference in ion concentration between the two solutions is quantitatively translated into a particular electrical potential that may be measured by an electrode, typically in units of millivolts (mV).

The measured potential is thus used to determine the ion concentration. In many sensors this determination is based on a theoretical ideal relationship between concentration of an ion and the electrical potential created by such a concentration. This is shown as line T (theoretical) in FIG. 1. Devices that base their measurement on the theoretical ideal electrical potential are thus useful only to the extent that the actual measurement is within an acceptable error range of the ideal. The difference between the actual measured potential and the theoretical ideal is a measure of the efficiency of the electrode. A large deviation between the actual and the ideal (inefficiency) renders the sensor unreliable or, in the extreme, useless.

Several factors may contribute to sensor inefficiency. For example, many membranes have a predictable rate of decay when in contact with an aqueous (water-based) ion solution or gel. In most devices, this decay may cause an unacceptable inefficiency within about two weeks. Thus, sensors of that type have a shelf life of less than two weeks between manufacture and use.

Another factor that affects sensor inefficiency is the imperfection of the membrane material, even before any degradation caused by aging. That is, because of the physical limitations of any given membrane, perfect efficiency never exists. For example, in a particular use, a 5% error may be deemed to be the largest acceptable error. A particular production batch of membrane may be tested and found to be 3% away from the ideal, before any degradation occurs in the membrane material.

If the inefficiency is constant across the useful range of ion concentration, the 3% difference of this example may be factored into a compensation formula, which would shift the intercept of the ideal line T, without affecting its slope, to yield the actual electrical potential per ion concentration line A (actual) as shown in FIG. 1. (Note that in the Figures, the graphs are drawn for general illustrative purposes, and are not drawn to any particular scale.) However, the inefficiency may not be constant across a concentration range, but may instead increase or decrease with increasing concentration, i.e., the relationship between electrical potential and ion concentration may be nonlinear. In these cases, there is no simple way to adjust for the inefficiency without further calibrating each membrane batch and adjusting the sensor's conversion ratios accordingly, if possible.

However, even in cases where the quality of the membrane material may be determined and adjusted for, deterioration of the sensor still occurs over time, and such deterioration must be accounted for in addition to the initial properties regarding the imperfections of the sensor. Thus, the disadvantages of existing sensors are evident: a very short shelf life and inaccurate, insensitive measurements.

Accuracy and sensitivity of a sensor are both affected by the deviation between actual and ideal correspondence of measured electrical potential to ion concentration. Clearly, if a sensor is inefficient to a given degree, this has a direct effect on accuracy of its readings. Likewise, the mere fact of having to allow for such an inefficiency introduces an error rate, and measurements that differ by less than the built in error rate are thus not discernibly different. In contrast, in a sensor which would be capable of self-monitoring and calibration, there would be no need to factor in error rates due to degradation or membrane inefficiency, since those values themselves, if determinable, could be used to calibrate the sensor just prior to its use.

SUMMARY OF THE INVENTION

One aspect of the invention is a sensor. In this embodiment, the sensor includes a sample receptacle and a data storage device, wherein the data storage device has data for calibrating the sensor and wherein the sensor includes one or more electrical contacts adapted for communication with a sensor data reader.

Another aspect of the invention is a single use sensor for determining the ionic strength of a sample. In this aspect, the sensor includes: a first half cell having a first precalibrant composition of a first ion species of a known concentration, and a first electrode in contact with the precalibrant composition; a second half cell including a reference composition of a known ion concentration, and a second electrode in contact with the reference composition; an ion selective membrane disposed between the first half cell and the second half cell; a conductive material in contact with the first half cell and the second half cell so that an electrical potential is formed across the ion selective membrane; and an electronic memory device electrically connected to the first electrode and the second electrode, wherein the electrical potential provides power to the electronic memory device.

Yet another aspect of the invention is a method of calibrating a sensor, comprising: providing a sensor including a data storage device and a plurality of half cells, wherein one of the half cells comprises a precalibrant solution having an electrochemical potential, and wherein the sensor is adapted to receive a sample comprising one or more species to be detected; obtaining data from the data storage device; analyzing the data to determine a present efficiency of the sensor; measuring the electrochemical potential of the precalibrant; and calibrating the sensor based on the electrochemical potential and the present efficiency.

Still another aspect of the invention is a method of quantifying the ion concentration of a sample in a sensor. In this aspect, the sensor includes a data storage device, a precalibrant composition and a reference composition. The method includes transferring data from the data storage device on the sensor to a sensor data reader; determining a first electrical potential between the precalibrant composition and the reference composition; calculating a calibration slope of electrical potentials and ion concentrations based on the first electrical potential and the data from the data storage device; measuring a second electrical potential between the reference composition and the sample; and quantifying the ion concentration of the sample based on the calibration slope and the second electrical potential.

DETAILED DESCRIPTION OF CERTAIN EMBODIMENTS

Disposable, precalibrated in vitro diagnostic sensors must possess sensitivity and precision equal to desk-top analyzers, and must, at the same time, ensure single-use, for the sake of safety, economics, and satisfaction of FDA requirements. To be practically useful, such disposable sensors should also possess a long shelf life. The present invention provides a new technology which integrates inexpensive, disposable semiconductor-based processors or other information storage devices with disposable, precalibrated ion-selective electrodes, such as those disclosed in U.S. Pat. No. 5,098,545, (the '545 patent) issued to Patko on Mar. 24, 1992, which is hereby incorporated by reference. This unique integration provides a novel and highly successful way of providing the special characteristics required.

Unlike any other product, the present invention provides disposable sensors that undergo a two point calibration just prior to use. Thus, the present invention has succeeded in instantaneously determining the initial sensor slope (line A) just milliseconds before sensor use in an equivalent of the two point calibrations of the more complex, non-disposable devices. This improvement dramatically improves sensitivity, precision, and shelf-life.

Figure 1:
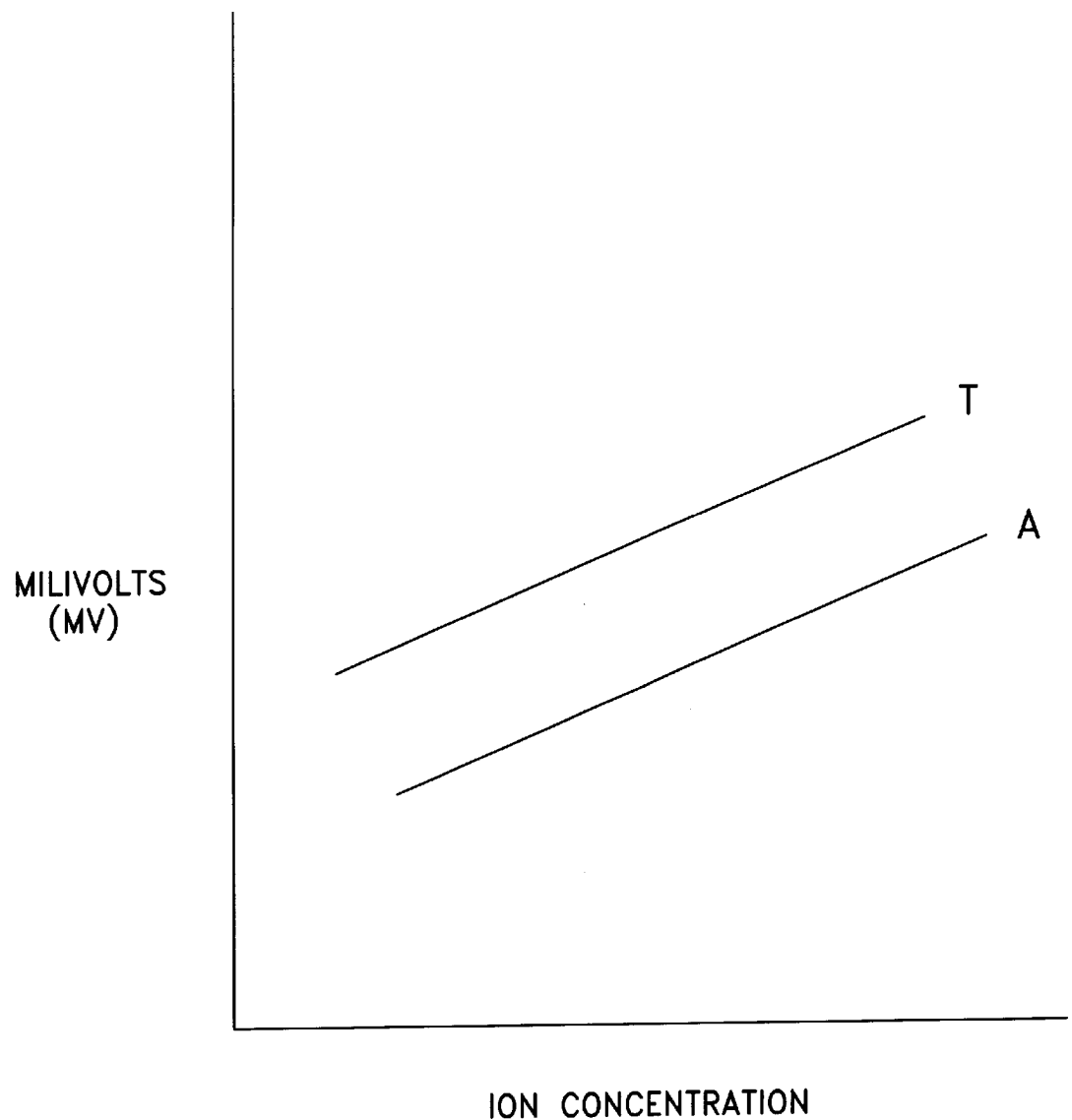
FIG. 1 is a graph illustrating the relationship between ion concentrations and electrical potentials measured in millivolts. The theoretical relationship of a sensor is shown as line T while the actual relationship of a sensor including sensor inefficiencies is shown as line A.
Figure 2:
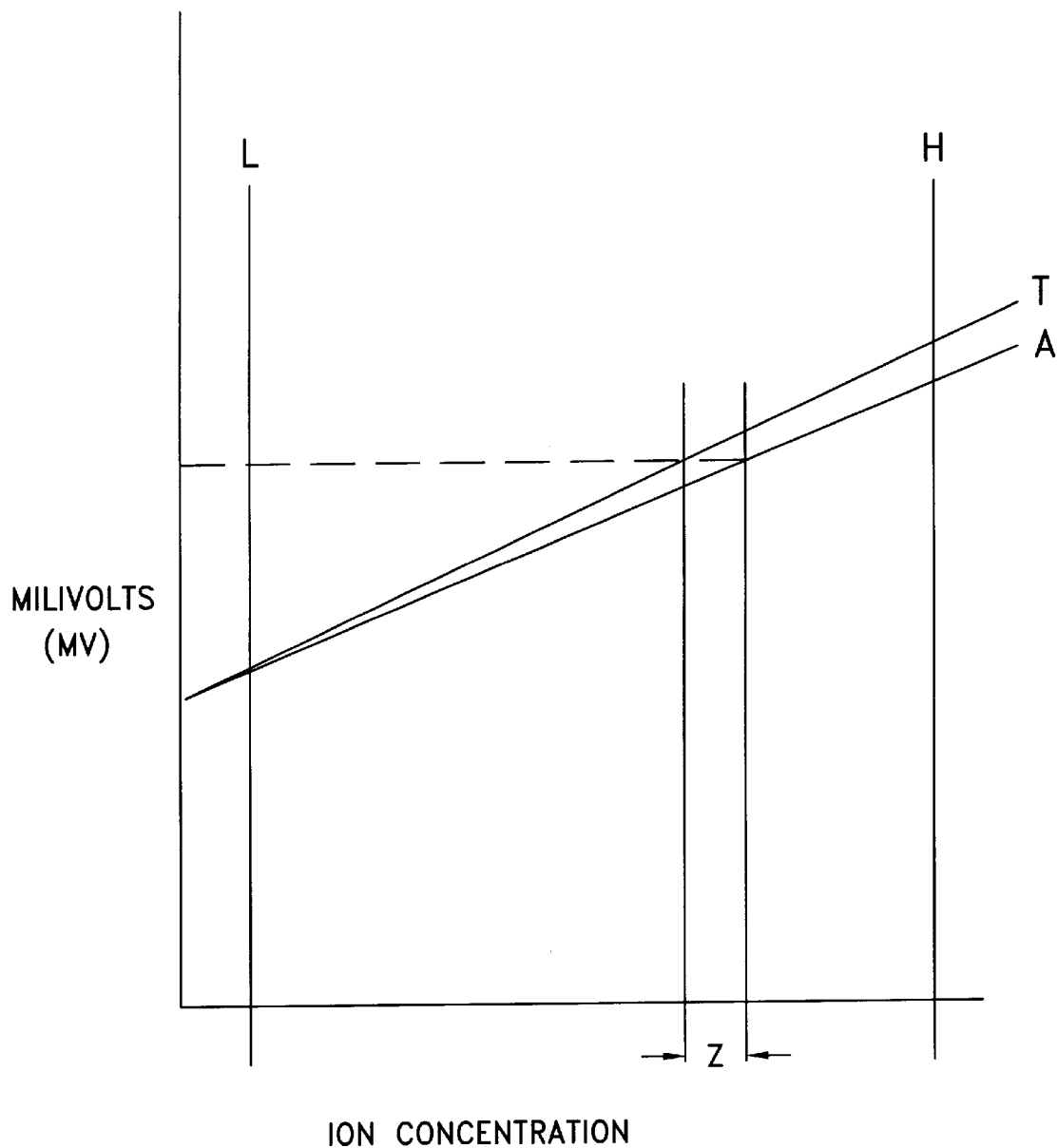
FIG. 2 is a graph illustrating the relationship between ion concentrations and voltage potentials. Theoretical slope T and actual slope A are shown to cross two other lines L and H, depicting the Low and High limits, respectively, between which the sensor's measurements of ion concentrations are expected to fall. Z indicates the differential ion concentration calculated between the theoretical and actual calibration slopes at a given voltage measurement.

The principle of deriving an ion concentration from a measured potential is illustrated in FIG. 2. Line T depicts the theoretical relationship between electrical potential and ion concentration. The slope of line T can thus be programmed into a sensor data reader, which measures the potential and then calibrates an ion concentration corresponding to that potential based on the slope of line T. This line is theoretical in that it is not based on any data points measured by or defined in terms of the actual properties of the sensor, but is instead based on the assumption that the electrode is 100% efficient. Line T is shown to cross vertical lines L and H, which depict the low and high limits, respectively, between which the sensor's measurements of ion concentration in the test sample will be expected to occur.

Clearly, if the inefficiency of the electrode produces a potential that is lower than the theoretical potential, the data points measured by the electrode will lie along the "actual" line A, and differences between lines T and A will cause underestimation of the ion concentration, introducing an error, Z, as shown in FIG. 2. The present invention includes a sensor that generates a true or actual line, corresponding to line A in FIG. 3, by tracking the electrode's deviation from perfect theoretical efficiency. This sensor is therefore capable of setting a point along line H that takes into account the empirically determined properties of the sensor, including the initial inefficiency of the sensor and the of the sensor thereof over time. This property then makes it possible for the sensor to "locate" and use point (h,a) instead of point (h,t). The sensor also has a self calibration capability that accurately locates point (l,a) just moments prior to the measurement of the test sample.

Because the sensor can determine both points (h,a) and (l,a) with great precision, the sensor can calculate the slope of line A (which may be constantly changing due to degradation of the membrane) at the precise moment of measurement. This virtually eliminates the error rate, and thus greatly enhances the accuracy and sensitivity of the sensor. In addition, the shelf life of the sensor of the invention is not limited by a predetermined "acceptable" error rate, as in other sensors. Instead, the shelf life of the sensor is measured in years rather than days, because the sensor only "expires" when it no longer has sufficient efficiency for any reliable measurement, rather than when it no longer has an efficiency that is within a very small deviation from the theoretical ideal, which requires an arbitrarily short shelf life.

The sensor of the invention achieves these improvements in sensitivity, accuracy and shelf life by storing data relating to the initial efficiency, efficiency decay rate, and date of manufacture. This information, which is carried with the sensor, allows precise determination of point (h,a), which is essential to the real-time derivation of line A, the line depicting the actual slope to be used for determination of the ion concentration in the test sample to be measured. Of course, to derive line A, it is also necessary to accurately determine point (l,a). The sensor of the invention locates this point by performing a precalibration.

Figure 4:
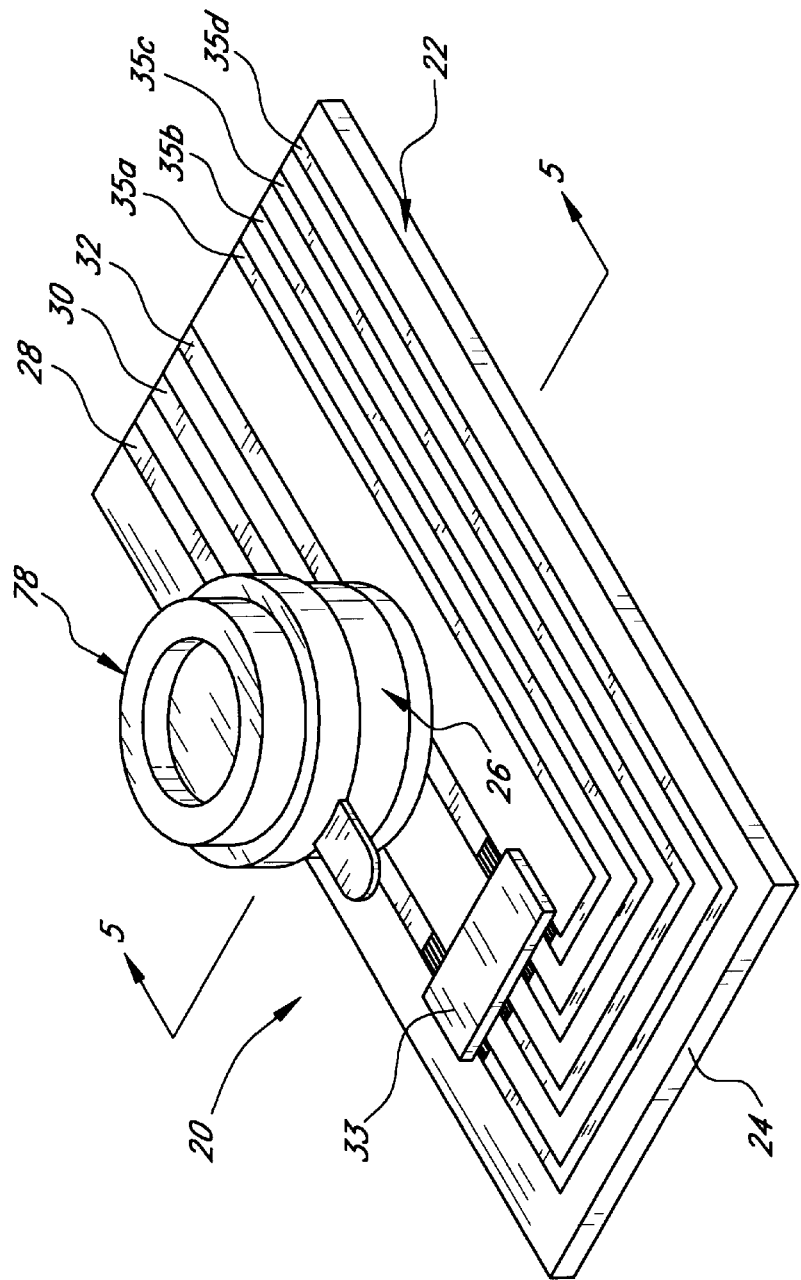
FIG. 4 is a perspective view of one embodiment of a sensor of the present invention.

The sensors in this description of the embodiments may be generally based on the sensor disclosed in the '545 patent. With reference to FIG. 4, a sensor device 20 contains in one half cell 82, also called the reference cell, a precalibrant composition 72, typically a solution or gel having a known ion concentration. When the sensor device 20 is inserted into a sensor data reader (not shown), points (h,a) and (l,a) are then calculated as follows: the reader scans information on a data storage device 33 carried on the sensor 20 that provides information on the initial efficiency, rate of decay, and date of manufacture of the ion-selective membrane 74. The reader then uses this data to determine precisely the present efficiency of the sensor device 20. This is the only information needed to determine point (h,a), by the following general formula:

$$E_p = E_i - (r_d \times t)$$

where $E_p$ is the present efficiency of the sensor, $E_i$ is the initial efficiency, $r_d$ is the rate of decay, and t is the time from manufacture to use.

Figure 3:
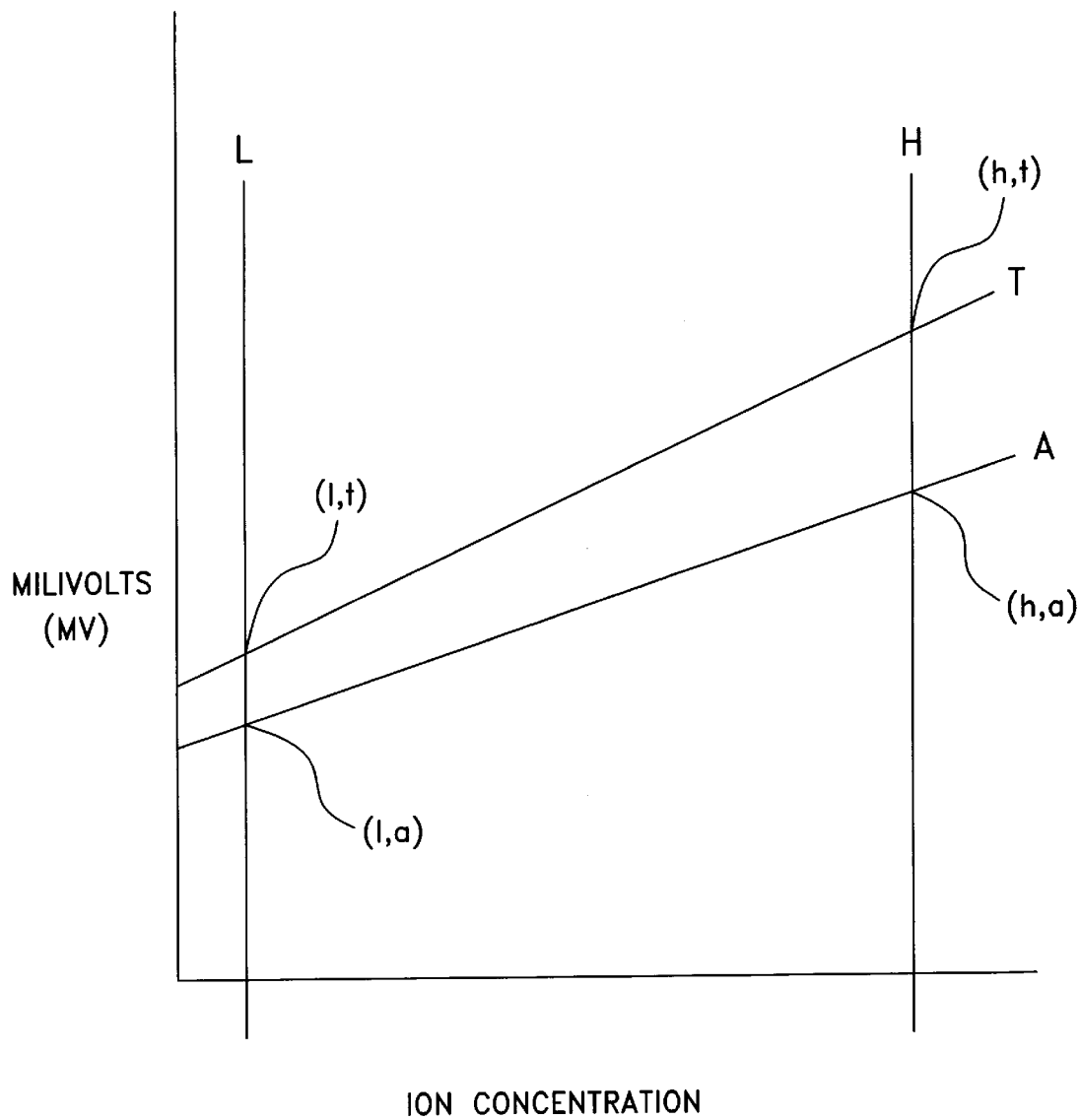
FIG. 3 is a graph illustrating the relationship between ion concentrations and voltage potentials. Theoretical slope T is shown to cross two other lines L (l,t) and H (h,t), depicting the Low and High limits, respectively, between which the sensor's measurements of ion concentrations are expected to fall. The actual slope A is shown to cross the low limit line L at (l,a) and the High limit line H at (h,a).

$E_i$ and $r_d$ are values that are empirically determined for each production batch of the ion-selective membrane 74 used in the sensor 20, and these values are stored, along with the date of manufacture, in the data storage device 33 of the sensor 20, to be read by the reader. A date function in the reader allows determination of t by subtracting the date of manufacture from the date of the reading. When $E_p$ is calculated from these data, it indicates how far down from point (h,t), along line H, the point (h,a) is located as shown in FIG. 3.

The reader determines point (l,a) by measuring the potential across the membrane 74 between the reference half cell 80 and a precalibrant half cell 82. Since the ion concentration in the precalibrant half cell 82 is a known quantity, the measurement of the potential precisely determines the position of point (l,a). The ion concentration of the precalibrant composition 72 may be stored as information in the data storage device 33 of the sensor 20, along with the other data mentioned above. In the alternative, the ion concentration of the precalibrant composition 72 may be constant for all sensors to be read by the reader, and may thus be information contained in the reader and not on the sensor device 20.

In certain embodiments of the present invention, the sensor 20 may contain multiple half cells 82 determining the concentration of two or more different analytes, and may employ as many different ion-selective membranes 74 as necessary. For example, sensors capable of multiple measurements are disclosed in the '545 patent. In such cases, the data storage device 33 on the sensor 20 may contain separate information for each membrane incorporated into the sensor 20. That is, for each membrane 74 in the sensor 20, values for $E_i$, $r_d$, and date of manufacture may be contained in the data storage device 33, allowing determination of a point (h,a) for each of the analytes to be measured. Likewise, for each analyte, a separate precalibrant composition 72 may be used, allowing precise determination of a point (l,a) for each analyte. Thus, whether the sensor of the invention is to be used for one or several analytes, the slope of line A can be determined for each analyte, thus eliminating any need to rely on theoretical slopes and further eliminating the problems of short shelf life and lack of accuracy and sensitivity associated therewith.

Determining the concentration of non-ionic analytes may, for instance, be performed by using the membranes disclosed in co-pending U.S. patent application ser. No. 09/055,815 filed Apr. 6, 1998, which is hereby incorporated by reference.

In one embodiment, all of the relevant information is communicated between the sensor 20 and the reader when the sensor is inserting into the reader, and the precalibration is automatically performed. When these actions are completed, the user removes a protective cap 78 and a conductive fill material 76 from a housing 26 on the sensor device 20, and applies a sample to a sample accepting depression 60 in the housing 26.

FIG. 4 is a perspective view of one embodiment of an electrochemical sensing device or sensor 20. This sensor device 20 includes an elongated, substantially flat, electrically non-conductive bottom member or plate 22 which serves several functions. Normally this member 22 may be either a common printed circuit board or a separate part formed by common injection molding techniques. It has a tab or tab-like end portion 24 which is intended to be used in manipulating the sensor device 20 for reading data. It also serves to support the cylindrical housing 26 which, together with the various parts located in and on the sensor device 20 forms the primary functional sensor "unit" (not separately numbered) of the entire sensor device 20.

The member 22 also serves to support three electrically conductive strips 28, 30 and 32 which extend along one another from an end 34 of the member 22 remote from the tab 24 to beneath the housing 26 where these strips 28, 30 and 32 are connected as subsequently described. As can be imagined, the end 34 preferably terminates in a series of electrical contacts for connecting the sensor 20 to a sensor data reader. The strips 28 and 32 also extend from beneath the housing 26 to provide electrical power to a data storage device 33. Extending from the data storage device 33 are a series of data lines 35a, 35b, 35c, and 35d that run to the edge 34 of the member 22. Although four data lines are shown, any integer member of N lines greater than or equal to one may be used.

The strips 28, 30 and 32 and data lines 35a–d can be formed as any other conductors on a printed circuit board or can be formed out of a conventional electrically conductive adhesive polymer composition. The strips and lines may be sufficiently abrasion resistant so that they can be used as prongs on a common electrical plug to connect the entire sensor device 20 to an appropriate electronic device (not shown) or used with the sensor device 20 to make measurements, determinations or analyses using the sensor device 20.

Suitable sensor data readers for use with the sensor device 20 are known, however, they may need to be modified to accept the data input lines 35a–d from the sensor device 20. Although the strips 28, 30 and 32 and data lines 35a–d can be connected to a sensor data reader using conventional techniques (not shown) such as wires and spring biased conductive clips it is preferred to make the member 22 sufficiently stiff so that a user, by holding the tab 24, can insert a portion 36 of the member 22 located between the housing 26 and the end 34 into an appropriate, conventional female socket (not shown) on the sensor data reader. As a result of this, the portion 36 of the member 22 can be referred to as a connector or male connector.

Figure 5:
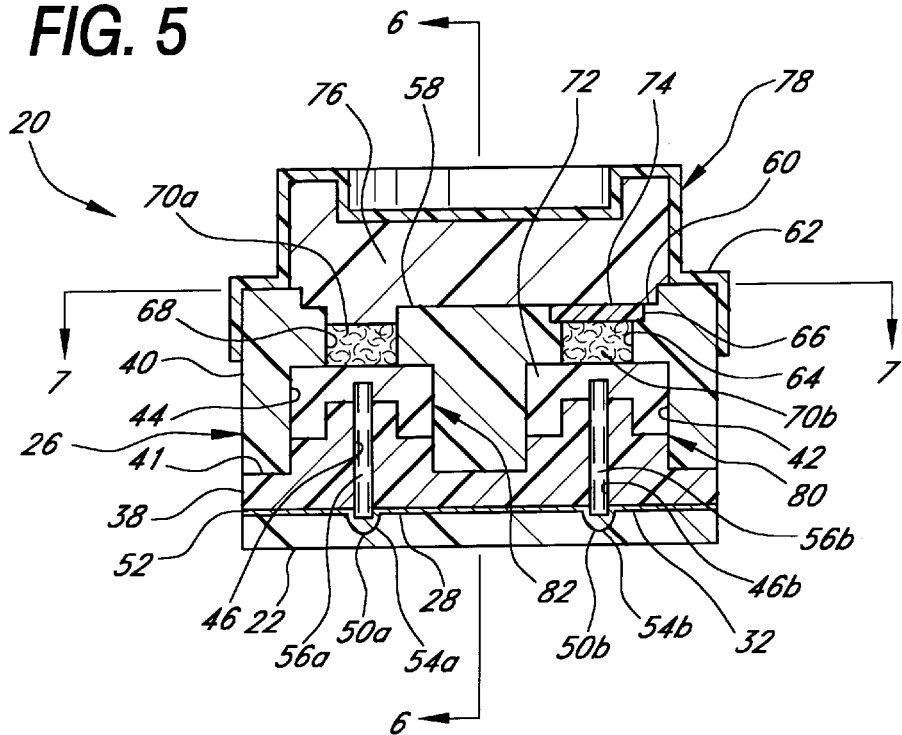
FIG. 5 is a cross-sectional view of the sensor shown in FIG. 4 taken along line 5—5.

As indicated in FIG. 5, the housing 26 on the device 20 is essentially a small, short cylinder. As manufactured, the housing 26 is formed of two separate electrically non-conductive components—a base 38 and a top 40—which are shaped as subsequently described. The components 38 and 40 can be easily formed out of common polymers by conventional injection molding techniques. As formed they have adjacent surfaces 41 which are normally secured together by any convenient manufacturing technique such as ultrasonic welding or the use or an inert adhesive (not shown). The components 38 and 40 are shaped so that as they are secured together along the surfaces 40 they define two separate internal cavities 42 and 44 within the housing 26.

Figure 6:
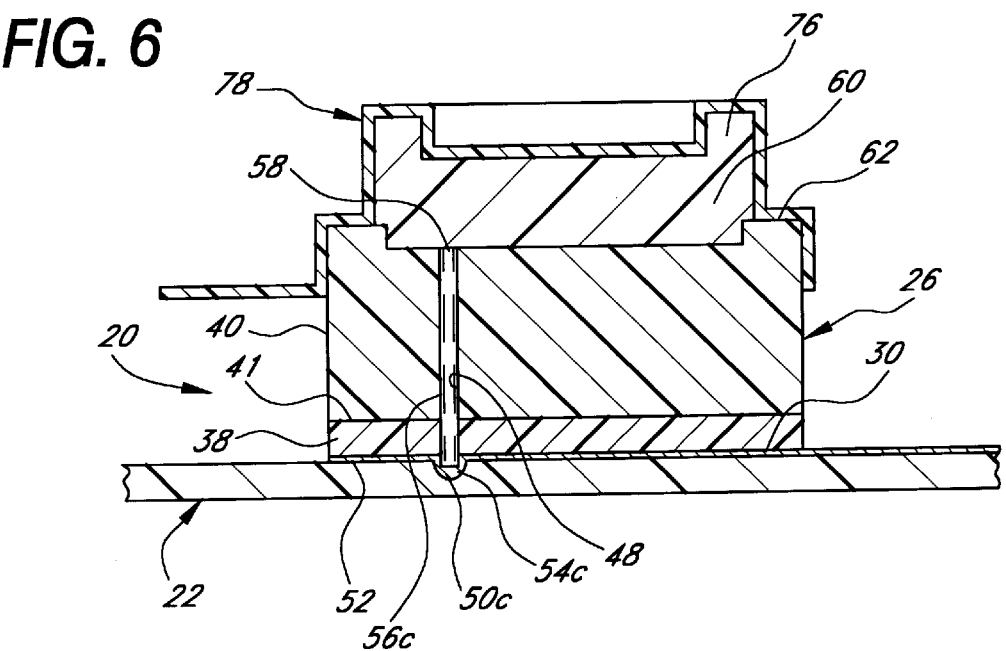
FIG. 6 is a cross-sectional view of the sensor of FIG. 5 taken along line 6—6.

The base 38 is shaped so as to include two elongated, vertically extending passages 46a, 46b extending into the cavities 44, 42, respectively. As indicated in FIG. 6, both the base 38 and the top 40 are shaped so as to include a third elongated, vertically extending passage 48. The passages 46a, 46b and 48 are located so as to be immediately above small depressions 50a, 50b, and 50c formed in the member 22. Except where the depressions 50a,b,c are located, the base 38 is attached directly to the member 22 so as to overlie the strips 28, 30 and 32 through the use of a small layer 52 of a conventional electrically nonconductive adhesive. Various functional equivalent techniques such as ultrasonic welding can also be used to secure the housing 26 in place on the member 22.

Figure 7:
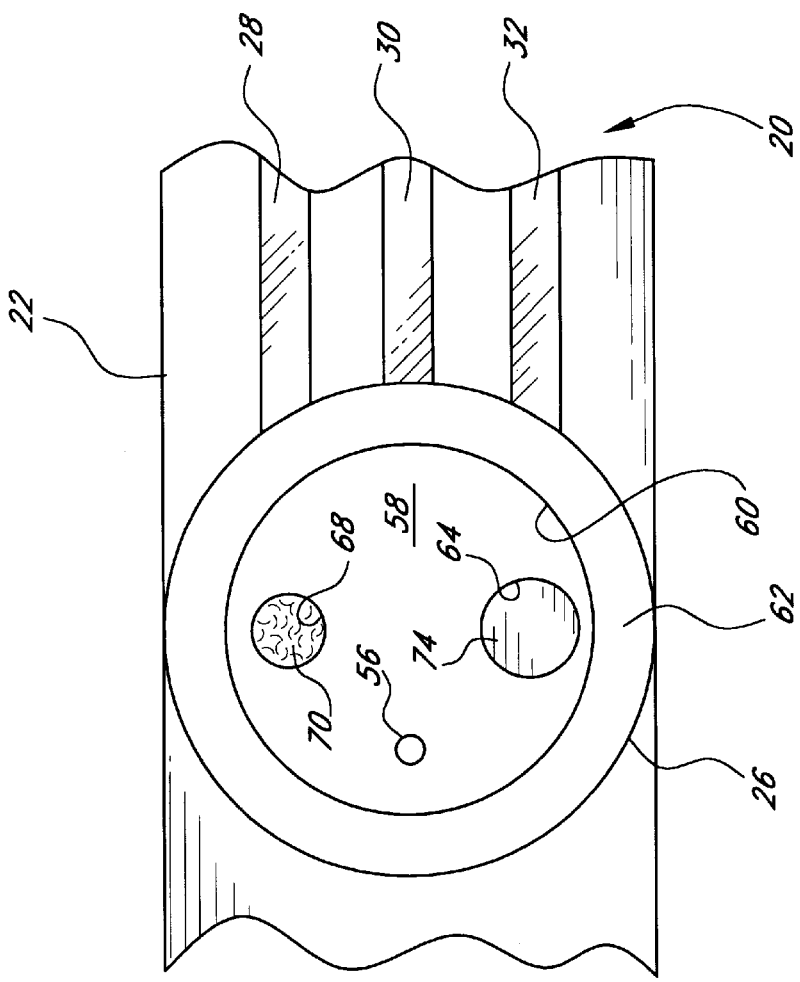
FIG. 7 is a cross-sectional view of the sensor of FIG. 5 taken along line 7—7.

The depressions 50a, 50b, and 50c intersect the strips 28, 30 and 32; they are used to hold small portions 54a, 54b, and 54c of a conventional electrically conductive polymer composition so as to electrically connect the strips 28, 30 and 32 to individual electrodes 56a, 56b, and 56c located in each of the passages 46a,b and 48. Other equivalent manners of establishing electrical connection between these parts can, of course, be employed. These electrodes 56a, 56b, and 56c can be press-fitted in place or can be secured in position through the use of a conventional adhesive (not shown). When they are secured in place, the electrodes 56a, 56b in the passages 46a, 46b extend upwardly into the cavities 42 and 44 while the electrode 56c extends through the passage 48 so as to be exposed to the bottom 58 of an enlarged, flat, disc-like depression 60 in the upper surface 62 of the top 40. Because of the shape and configuration of this depression 60 it may be regarded as a sample container or sample receptacle. This can be seen more clearly in reference to FIG. 7.

Referring back to FIGS. 4 and 5, a stepped hole 64 having an upwardly facing shoulder 66 is located in the top 40 so as to lead downwardly from the depression 60 into the cavity 42. Another hole 68 is located in the top 40 so as to lead downwardly from the depression 60 into the cavity 44. The hole 64 below the shoulder 66 and the hole 68 are both filled with identical porous, electrically non-conductive plugs 70a, 70b. These plugs 70a,b may be considered as flow restricting members or membranes. They may be press-fitted into place or may be secured in position through the use of an appropriate conventional adhesive (not shown). Both of these plugs 70a,b and the cavities 44 and 42, respectively beneath them are filled with an electrolyte composition 72 as indicated in the ensuing text. In addition, a small, comparatively thin membrane or barrier 74, as later discussed in this document, is secured in place in a similar manner in the hole 64 against the shoulder 66.

The composition of the membrane 74 is quite important in connection with the sensor or sensing device 20. When this sensor 20 is to be used in detecting a specific ion species, this membrane 74 should be selective relative to such ion. Similarly if the sensor 20 is to be used in detecting and measuring two or more closely related ions the membrane should be selective in connection with all of such ions. Non-limiting examples of some ions that can be selected using an ion selective membrane are: calcium, chloride, hydrogen, lithium, magnesium, potassium, sodium, ammonium ($NH_4$,) Ag (silver), As (arsenic), Pb (lead), plus the anion $NO_2$ (2-), nitrate $NO_3$ (-), and cyanate.

A selective material in the membrane 74 should be of a character which is such that it can be used in accordance with conventional electrochemical practice so as to detect the presence or absence of an ion or such related ions in a fluid and, if such an ion or such ions are present, so as to provide an indication of the amount of such ions present in the sample. Similarly, if the sensor 20 is to be used to detect the presence of a gas or related gases in a sample and, if such a gas or gases are present, to provide an indication of the extent of such presence the membrane 74 should be of a type recognized in the membrane technology as effective for such purpose. Because of the fact that suitable compositions for use with ions and gases are known and because of the fact no specific membrane or barrier material is required, the membrane 74 will not be described.

For the same reason, it is not considered necessary to describe specific electrolytes or electrolyte compositions for use as an electrolyte composition 72. Although different types of compositions could be used in the cavities 42, 44, it is preferred that only one electrolyte composition 72 be used in both of the cavities 42, 44 and in both of the plugs 70a,b. It is further preferred that the same composition be used in forming a fill material 76 which fills the depression 60 and which lies against and covers the plug 70 which is exposed to the cavity 60 and the membrane 74.

Although it is not necessary to use the fill material 76 with the sensor 20 as subsequently indicated it is preferred to employ it in connection with this sensor 20. Although it would be possible to achieve benefits in accordance with the invention if such a composition 72 was a liquid composition of a known or conventional character used in connection with ion and gas selective electrochemical measurements for a practical reason it may be preferred to use a gelled electrolyte composition instead of such a liquid electrolyte composition.

This is because of the fact that a liquid is apt to flow out of any of the locations discussed during packaging, handling and use of a sensor 20 whereas a gelled electrolyte under the conditions to which a sensor 20 will be subjected will not normally flow from any location in which it is located. It is considered that gelled ion and gas selective electrolytes are well known. Hence, it is not considered necessary to discuss them in detail in this specification. Normally they will be prepared by adding a suitable gelling agent such a polyacrylamide or other known polymer composition which will cross-link on gelling to a liquid electrolyte and then placing the electrolyte in a desired final location before the gelling agent causes a gel to form.

The cavities 42, 44 and the plugs 70a,b can be filled concurrently by vacuum impregnation with the composition 72 before it has gelled prior to the membrane 74 being located in its final position. Then, after the membrane 74 has been located in place, by casting some of the same composition 72 in the depression 60 so as to create the fill material 76. It will be recognized that there can be considerable variation in both the composition of the electrolyte used as the composition 72 and in forming the fill material 76. In effect the latter really should also be referred to as an electrolyte composition because of its function.

The electrolyte composition 72 and the fill material 76 have preferably the same or substantially the same electrochemical characteristics. Obviously when the composition and the fill material 76 all have exactly the same ingredients this is the case. When the composition 72 and the fill material 76 are the same there will be no ion movement within or between the composition and the fill material 76 since there is no ion concentration differential present. Substantially the identical considerations are involved in connection with electrolytes for use in gas analysis. As a consequence, the sensor 20 can be precalibrated prior to its being delivered to or used by an ultimate user. As subsequently discussed, such a user need only to remove the fill material 76 and to substitute a sample or specimen (not shown) in making a desired determination.

As supplied to a user, the device typically includes a small impervious, polymer protective cover or cap 78 which fits tightly against the top 40 so as to close or seal off the depression 60 from ambient environmental influences. Although this cap 78 can be held in place merely by press fitting tightly against the housing 26 it can also be held in place by a conventional tacky adhesive (not shown) or by a small, easily broken weld or seal (not shown). If desired the cap 78 and the fill material 76 can be secured together by a mechanical interlock (not shown) or by a common adhesive (not shown) so that when the cap 78 is removed the fill material 76 will also automatically be lifted away from the housing 26.

Using the Sensor Device

When the sensor 20 as supplied to a user is to be employed it is necessary to perform a series of minor steps in order to prepare it for use. The sequence of these steps can be varied as desired. The sensor 20 may initially be plugged into a female socket of an electronic apparatus as discussed above. Next, the cover or cap may be removed from the housing 26 by simply being lifted or torn off of the housing 26. If the fill material 76 was not lifted out of the depression 60 when the cap 78 was removed, it can be removed from the depression using any convenient manipulative tool such as tweezers (not shown). At this point the device or sensor 20 is ready to be used.

As discussed previously, in some embodiments, removing the cap 20 will destroy the electrical power connection to the data storage device 33. Thus, if the data storage device comprises a volatile memory device, all of the data will be lost. This may be desired if a design goal is to ensure that the sensor device 20 is only used once. In this embodiment, after the cap 78 has been removed, all of the data is lost from the data storage device 33 so the sensor device 20 cannot be reused. In addition, one of ordinary skill in the technology could program the device that reads the sensor device 20 to produce an error if the data storage device 33 is blank.

As the sensor device 20 is used the first time, the depression 60 will be filled with a liquid sample or specimen to be examined. Because of the location of the depression 60 it will normally be relatively easy to fill it with a small quantity of the sample of a specimen. This filling of the depression 60 will place the liquid to be analyzed in direct contact with the membrane 74, one of the plugs 70*a,b* and the electrode 56. The plug 70*a* associated with the cavity 44 will tend to isolate such liquid from the electrolyte composition 72 within the cavity 44. Although to a degree the plug 70*b* associated with the other cavity 42 does this too, it primarily serves to reinforce or support the membrane 74 while concurrently isolating the liquid.

As a consequence of the support provided by the plug 70*b*, the membrane 74 can be comparatively thin and/or weak without there being significant danger of it being cracked or otherwise damaged. This is important for economic reasons since it makes it possible to minimize the material in the membrane 74. It may also be desirable for other reasons. When the depression 60 is filled, the liquid in effect bridges the cavities 42 and 44 similar to the way a conventional bridge used in prior electrochemical measurement devices extends between and connects two separate half cells.

In the sensor device 20, the cylindrical housing 26 acts as a common housing for the two half cells 80, 82 (FIG. 5). The half cell 80 includes the portions of the housing 26 surrounding the cavity 42, the electrode 56*b* extending into the cavity 42, the electrolyte composition 72 within it, the plug 70*b* associated with it and the membrane 74. This half cell 80 may be referred to as a sensing cell because the membrane 74 makes it possible to use this sensing half cell 80 to provide a signal indicative of the presence or absence of an ion or ions or a gas or gases in the specimen and if appropriate an indication of the quantity of the same present.

The second half cell 82 includes the portions of the housing 26 surrounding the cavity 44, the electrode 56*a* extending into this cavity 44, the electrolyte composition 72 within this cavity 44 and the plug 70*a* associated with it. This second half cell 82 may be referred to as a reference cell because it is used to provide a reference reading or signal indicative of the specimen.

To obtain the signals or readings from these two half cells 80 and 82, the sensor data reader into which the device or sensor 20 has been plugged is operated in a conventional manner. During this operation, the electrodes 56*a*, 56*b* extending into the depression 60 will be in contact with the liquid being analyzed and may be used as a ground in making accurate measurements in accordance with a technique not forming part of this invention. Since the general operation of an appropriate electronic apparatus is known, it is not described in detail in this document.

The sample is thus quantitatively analyzed for the ion(s) of choice, and the voltage in mV is converted to indicate the concentration of the ion(s) by fitting the measured potential to line A, which is defined by points (l,a) and (h,a). The reading thus obtained is far more sensitive and accurate than is possible using existing sensors, even in conditions where the sensor 20 of the invention has aged several months or years.

The presence of the relevant data in the data storage device 33 of the sensor 20 allows these vast improvements in performance and shelf life. The data relating to the sensor device 20 can be stored in various ways. Non-limiting examples are data storage by bar-code, non-volatile memories, volatile memories, electro-optical media, digital storage media, magnetic strip, data embossing, and holograms.

In the bar-code embodiment of the invention, each sensor device 20 is labeled with a bar-code that contains the information necessary to derive line A of FIG. 3, as described above. The bar-code, or any of the other modes of data storage, may also contain other information such as, for example, a serial number unique to each sensor to prevent reuse thereof, coded information to tell the reading device what kind of ion is to be measured by that particular sensor, quality control information, and the like.

The unique serial number prevents reuse in an embodiment wherein the sensor data reader has a memory function that records the serial number of each sensor unit read and refuses to read any unit more than once. In other embodiments, the reader may simply remove or destroy data stored in a semiconductor memory, at some point between insertion of the sensor into the reader and removal therefrom. Guaranteeing single use of each sensor may be essential for certain medical uses of these sensors and also prevents problems of quality control that could otherwise occur with improper cleaning and reuse of the sensor.

In the non-volatile memory device embodiment of the invention, the sensor 20 includes a non volatile data storage device capable of storing data and allowing the data to be retrieved by the reader without requiring any input of electrical energy during the time the data are stored. Suitable memory devices for use in this embodiment of the invention include, for example an EEPROM, EPROM, static memory, bubble memory, PAL or other similar data storage device that can store data without being electrically refreshed.

In this embodiment, single use can be assured by providing a function in the reader that erases or otherwise degrades or destroys the data stored in the non-volatile data storage device 33 while the sensor is in the reader. Such a deletion of data can be achieved, for example, by overwriting the data stored in the non-volatile memory device with a series of ones or zeros. A data deletion can be performed, for example, in an embodiment wherein the non-volatile data storage device 33 is an EEPROM, by triggering a signal that causes the EEPROM to electrically erase its data. Also, as in the bar code embodiment, each sensor unit may simply be identified by a unique serial number stored in the non-volatile memory device, and the reader may be programmed not to accept a sensor that has been previously read.

In an embodiment wherein the data storage device 33 comprises a volatile memory device, the relevant data are stored on a memory device that requires a consistent electrical refresh cycle to maintain the data. If the volatile memory device loses power, all of the data stored will be lost. Suitable memory devices for use in this embodiment of the invention include, for example, dynamic random access memory (DRAM) and static random access memory (SRAM). In this embodiment, the energy required to refresh the volatile memory device is provided by the electrical potential existing between the precalibrant half cell 80 and the reference half cell 82. The energy demands of volatile memory devices are normally so small that the nature of the precalibrant medium would not be significantly changed even over several years of storage of the sensor. Thus, the precalibration cells of the sensor can effectively function as a battery to maintain the data on a volatile data storage device 33.

Automatic Calibration of the Sensor

In use, the sensor 20 is inserted into the reader, which determines the position of point (h,a) by reading the data stored in the data storage device 33 relating to the initial efficiency of the sensor, rate of decay, and date of manufacture. The reader thereafter performs a precalibration calculation by measuring the electrical potential across the membrane 74 between the precalibrant half cell 80 and the reference half cell 82. The electrical potential in millivolts is used to determine the position of point (l,a) (FIG. 3).

When these calculations are completed the reader indicates to the user that the calibration curve has been determined. The user then removes the cap 78 and fill material 76 from the housing for placement of the sample. In one embodiment, removal of the cap 78 and fill material 76 also breaks the connection between the precalibrant half cell 80 and the reference half cell 82, which cuts off power to the data storage device 33, clearing it of data. Thus, the single use of the sensor 20 in this embodiment of the invention is guaranteed by mere removal of the cap 78 and fill material 76, without requiring any additional action of the reader to delete or replace the information stored on the volatile data storage device 33.

In another embodiment, the data storage device 33 is in communication with a microprocessor (not shown). The microprocessor may be programmed with software code stored in the microprocessor or in a separate data storage device such as the device 33 to repetitively calculate the location of point (h, a), based on the initial properties of the sensor and the time since manufacture. Thus, it becomes unnecessary for the reader to make this computation. The sensor 20 itself, having a built in microprocessor, can perform some or all of the computations required to correctly place both calibration points (h, a) and (l, a) and to convert the measured potential to indicate the ion concentration in the sample to be measured. The invention thus encompasses sensors with built-in microprocessors, having processing capabilities ranging from the basic computations required to position point (h, a) to the full set of computations necessary to calibrate the sensor and measure the ion of interest. Both the volatile and non-volatile data storage devices may be used in aspects of this embodiment of the invention.

Furthermore, the microprocessor or hard-coded digital logic may be incorporated with the memory in a single chip package such as an application specific integrated circuit. It will be understood that the hardware and software partitioning on the sensor, the reader, and between the sensor and reader may be designed in a multitude of ways.

While the foregoing Detailed Description and Examples disclose certain preferred embodiments of the invention, the invention also includes numerous other embodiments. The invention is thus to be limited only by the scope of the following claims.

What is claimed is:

1. A sensor, comprising:

a sample receptacle;

a data storage device comprising a volatile or non-volatile electronic memory device wherein said data storage device stores data for calibrating the sensor and wherein the sensor comprises one or more electrical contacts adapted for data communication with a sensor data reader;

a plurality of half cells forming a battery for providing electrical power to the volatile or non-volatile electronic memory device; and a conductive material disposed between the half cells such that removal of the conductive material disrupts the electrical power to the electronic memory device.

2. The sensor of claim 1, wherein the electronic memory device is volatile and data stored in the volatile memory device is lost upon removal of the conductive material.

3. The sensor of claim 1, wherein the conductive material is a conductive gel disposed in the sample receptacle.

4. A method of calibrating a sensor, wherein the sensor comprises a data storage device and a plurality of half cells, wherein one of the half cells comprises a precalibrant solution having an electrochemical potential, and wherein the sensor is adapted to receive a sample comprising one or more species to be detected, the method comprising:

obtaining data from the data storage device;

analyzing the data to determine a present efficiency of the sensor;

measuring the electrochemical potential of the precalibrant; and determining a calibration slope based on the electrochemical potential and the present efficiency.

5. The method of claim 4, wherein the data storage device is an electronic memory device.

6. The method of claim 5, further comprising overwriting or erasing the data from the electronic memory device after the data has been transferred to a sensor data reader, thereby preventing a second retrieval of the data.

7. The method of claim 5, wherein the sensor further comprises a microprocessor and software code to conduct the calibrating of the sensor.

8. The method of claim 5, wherein the electronic memory device is a nonvolatile electronic memory device.

9. The method of claim 4, wherein the data storage device comprises a bar code.

10. The method of claim 9, further comprising removing or destroying the bar code after a transferring the data to a sensor data reader, thereby preventing a second retrieval of the data.

11. A method of quantifying the ion concentration of a sample in a sensor, the sensor comprising a data storage device, a precalibrant composition and a reference composition, the method comprising:

a) transferring data indicative of an ion concentration from the data storage device on the sensor to a sensor data reader;

b) determining a first electrical potential between the precalibrant composition and the reference composition;

c) calculating a calibration slope of electrical potentials and ion concentrations based on the first electrical potential and the data from the data storage device;

d) measuring a second electrical potential between the reference composition and the sample; and e) quantifying the ion concentration of the sample based on the calibration slope and the second electrical potential.

12. The method of claim 11, wherein transferring data from the data storage device to the sensor data reader comprises transferring data from an electronic memory device to the sensor data reader.

13. The method of claim 12, further comprising the step of erasing the data stored on the electronic memory device after the data has been transferred to the sensor data reader.

14. The method of claim 12, wherein transferring data from the data storage device to the sensor data reader comprises transferring data from a bar code to the sensor data reader.

15. The method of claim 14, further comprising the step of destroying the bar code after the data has been transferred to a sensor data reader.

* * * * *